United States Patent [19]

Boumendil

[11] Patent Number: 5,017,189

[45] Date of Patent: May 21, 1991

[54] PROTECTIVE CAP FOR A HYPODERMIC SYRINGE

[75] Inventor: Frank Boumendil, Boulogne, France

[73] Assignee: Michel Gordon, Paris, France; a part interest

[21] Appl. No.: 471,520

[22] Filed: Jan. 29, 1990

[30] Foreign Application Priority Data

Feb. 3, 1989 [FR] France .................................. 89 01387

[51] Int. Cl.⁵ .............................................. A61M 5/32
[52] U.S. Cl. .................................... 604/192; 604/263
[58] Field of Search ................ 604/192, 187, 263, 162

[56] References Cited

U.S. PATENT DOCUMENTS

| | | |
|---|---|---|
| 2,854,976 | 10/1958 | Heydrich . |
| 3,537,452 | 11/1970 | Wilks .................................... 604/162 |
| 3,658,061 | 4/1972 | Hall . |
| 4,643,722 | 2/1987 | Smith, Jr. . |
| 4,883,469 | 11/1989 | Glazier ................................. 604/192 |
| 4,917,243 | 4/1990 | Abrams et al. .................. 604/192 X |

FOREIGN PATENT DOCUMENTS 3713754  11/1988  Fed. Rep. of Germany .

*Primary Examiner*—John D. Yasko
*Attorney, Agent, or Firm*—Young & Thompson

[57] ABSTRACT

The protective cap for the needle of a hypodermic syringe is constituted by a hollow body of elongated shape which is open at one end and provided over its entire length with an opening for the introduction of the needle. On the opposite side, the protective cap has a flat bearing face in order to place the cap on a flat surface in a stable manner. Flexible strips serve as members for locking the needle-mounting sleeve against the inner wall of the cap after it has been introduced. The protective cap is intended to enclose the needle of a hypodermic syringe before and after use.

4 Claims, 1 Drawing Sheet

PROTECTIVE CAP FOR A HYPODERMIC SYRINGE

BACKGROUND OF THE INVENTION

The present invention relates to a protective cap for enclosing the needle of a hypodermic syringe which may or may not be intended for medical use.

At the present time, a cap of this type is designed in the form of an elongated hollow body of circular cross-section, one end of which is closed whilst the other end is open so that it can be frictionally engaged on the conical sleeve provided at the lower end of the needle to be covered for the purpose of fixing it on the discharge nozzle of a syringe. Caps of this type can thus be readily removed when using the corresponding needles. However, they are intended to be put back in place after the needles have been used in order to guard against any danger of injury to a third party and above all any danger of contamination by the blood of the person who has been subjected to an injection, especially any danger of contamination by AIDS or serum hepatitis, etc.

However, the re-introduction of a hypodermic needle into a cap of this type is very difficult. In fact, the operator has to hold the cap with one hand while the syringe which carries the spent needle is held with the other hand. He then has to engage the end of this needle within the cap, or conversely. However, this operation is very awkward and the operator is very often unable to engage the needle within its cap. In point of fact, a faulty handling operation may result in accidental pricking and therefore in a risk of contamination of the operator. Under these conditions, members of medical staffs are more and more inclined to omit replacement of protective caps on hypodermic needles, thus entailing risks of contamination of third parties.

In an attempt to solve this problem, U.S. Pat. No. 4,643,722 relates to a protective cap having a slit which extends practically over its full length from its open end. This slit is intended to permit introduction of a needle on one side and not at the end. However, this is not sufficient to solve the problem at issue. In fact, in order to introduce a syringe needle into a cap of this type, the operator again has to hold this latter with one hand while holding with the other hand the syringe which carries the spent needle. In consequence, there is still a considerable danger of accidental pricking which arises simply from the fact that the operator has to hold the cap with one hand while inserting the needle in this latter.

Another problem which is not satisfactorily solved by U.S. Pat. No. 4,643,722 is that of complete enclosure of a spent needle within its protective cap. In fact, in order to remove any danger of contamination, the needle must be perfectly secured and completely enclosed within its protective cap. Now in order to close the longitudinal slit, U.S. Pat. No. 4,643,722 simply proposes to close the longitudinal needle-insertion slit by means of a member which is subsequently fitted on said slit. Positioning of this closure member is again a potential cause of accidental pricking of the operator if the needle moves during this operation. Moreover, the addition of a closure member of this type is a cause of complication, not only in regard to the operations to be performed but also in regard to the manufacture of the protective cap and its cost price which must remain extremely low.

For the reasons given in the foregoing, the present invention is directed to a protective cap which is intended to serve the same purpose but which is designed with a view to avoiding the disadvantages recalled above and in particular the risks of contamination of a medical practitioner or of a third party.

SUMMARY OF THE INVENTION

To this end, the invention is concerned with a protective cap for the needle of a hypodermic syringe provided with a mounting sleeve at its lower end, said cap being constituted by a hollow body of elongated shape which is open at one end and provided over its entire length with a longitudinal opening for the lateral introduction of a syringe needle through the corresponding side of said hollow body, said protective cap being distinguished by the fact that:

on the side opposite to said longitudinal opening, said elongated body has a flat bearing face which makes it possible to place said body on a flat surface in a stable manner, and that provision is made on each side of the longitudinal opening for flexible strips through which the spent needle of a syringe is allowed to pass at the time of introduction of said needle through the opening and which are then capable of closing the internal space of the protective cap in order to enclose the spent needle placed within said space.

It is thus an extremely easy matter to reintroduce a hypodermic needle into a cap of this type. For this operation, the cap can in fact be placed on a flat surface and it is then only necessary to introduce the needle above said cap and to engage it within the opening which extends over the entire length of this latter. At the time of engagement of the needle within the cap, the mounting sleeve which exists at the lower end of the needle momentarily separates the locking strips and these latter subsequently draw closer together so as to enclose the spent needle which is placed within the cap.

However, the main advantage of the cap in accordance with the invention lies in the fact that this latter does not have to be held in the user's hand at the time of introduction of a spent needle since it can be placed flatwise on any support during this operation. In consequence, this radically removes any risk of accidental pricking of the operator.

In an advantageous embodiment, the flexible strips provided on each side of the longitudinal opening of the cap are inclined inwards and are capable of exerting pressure on the mounting sleeve which exists at the lower end of a needle placed within said cap in order to apply said sleeve against the internal wall of said cap.

In addition to these inwardly inclined locking strips, the protective cap in accordance with the invention can advantageously be provided with two other flexible strips which cover said inwardly inclined strips and form a closure valve above these latter.

BRIEF DESCRIPTION OF THE DRAWINGS

Further distinctive features and advantages of the protective cap in accordance with the invention will become apparent from the following description of one example of construction, reference being made to the accompanying drawings, in which.

DETAILED DESCRIPTION OF THE INVENTION

Figure 1:
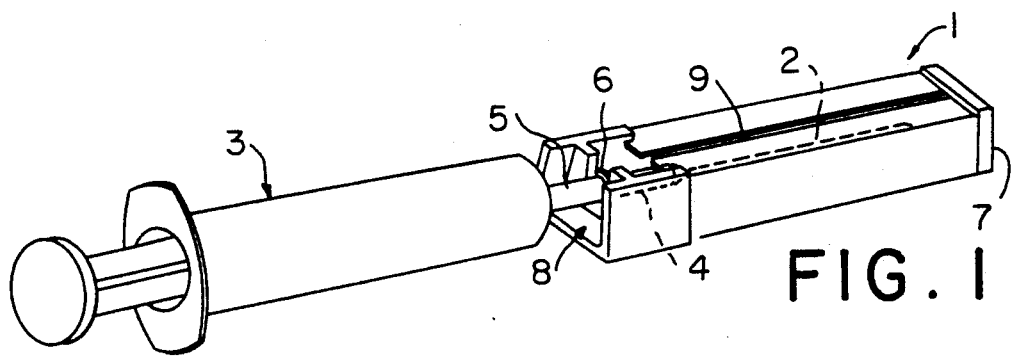
FIG. 1 is a perspective view of a hypodermic syringe having a needle which is enclosed in a protective cap in accordance with the invention.

As has already been mentioned, the protective cap 1 in accordance with the invention is intended to cover and to enclose a needle 2 which equips a hypodermic syringe 3. In the usual manner, said needle is provided at its lower end with a conical sleeve 4 which serves to mount said needle on a syringe of this type by fitting said sleeve on the discharge nozzle 5 of the corresponding syringe, said sleeve 4 being provided with an annular flange 6.

The cap 1 is constituted by a hollow body of elongated shape which is closed at one end 7 whilst its opposite end is freely open. In the example shown, said hollow body has a cross-section of trapezoidal shape, the long base of which corresponds to a flat face 8 which is intended to serve as a bearing surface on any flat support. On its opposite face which therefore corresponds to the short base of its trapezoidal cross-section, the cap 1 has a slit 9 which extends over its full length from its open end. On each side of said slit, provision is made for two flexible strips 10 which form a virtual closure valve. The elastic flexibility of said strips is obtained at the time of manufacture of the cap 1 by molding from a suitable plastic material.

Figure 2:
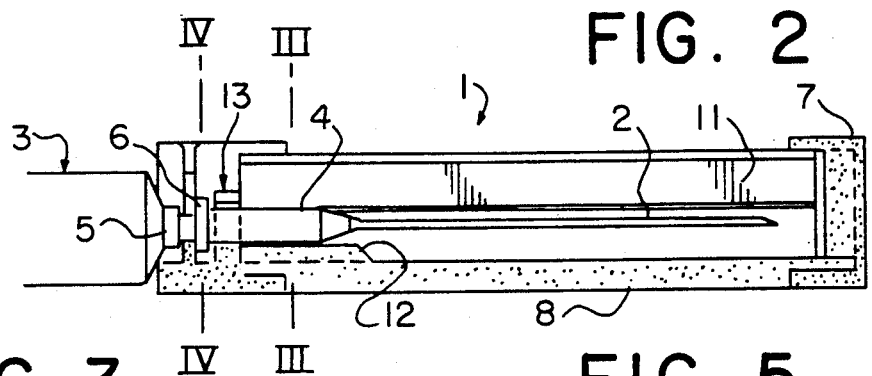
FIG. 2 is an axial sectional view of said protective cap.
Figure 3:
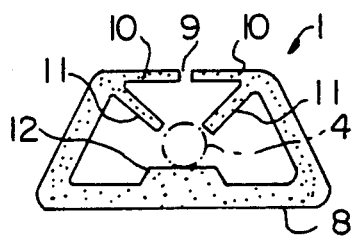
FIGS. 3 and 4 are transverse sectional views of said cap in transverse cross-section along the lines III—III and IV—IV of FIG. 2.

Beneath the two strips 10, provision is made for two other flexible strips 11 which are inclined towards the interior. When the needle 2 is in position within the cap, said flexible strips 11 serve as locking members for the sleeve 4 on which said needle is mounted. Said sleeve can then rest on a bearing plate 12 which is formed by molding on the internal face of the large cap face 8. As can be observed in FIGS. 2 and 3, the cap 1 is thus perfectly locked in position on the needle 2 and its sleeve 4 by virtue of the resilient pressure exerted on said sleeve by the two strips 11.

Figure 4:
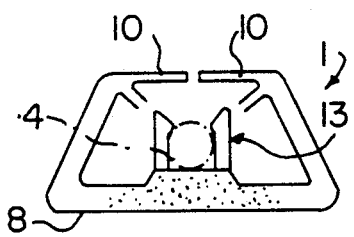
Figure 6:
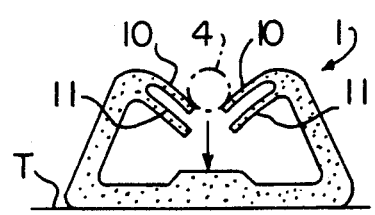
FIG. 6 is a perspective view illustrating the operation involved in putting a hypodermic needle back in position within a protective cap.
Figure 7:
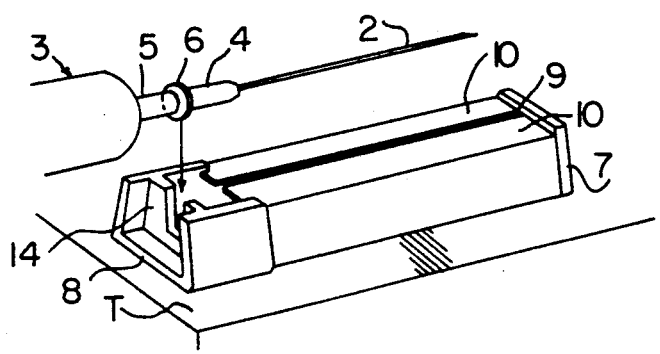
FIG. 7 is a schematic sectional view which is similar to FIG. 3 and which illustrates the same operation.

However, the cap 1 can be fixed in position even more securely by providing a resilient clip 13 at the entrance of said cap, said clip being so arranged as to fit resiliently on the needle-mounting sleeve 4 (as shown in FIG. 4). However, this resilient clip is not absolutely indispensable for fixing the cap 1 in position. In the form of construction shown, a partition 14 having a slot 15 is provided at the end of the cap opposite to its closed end 7. However, in this case also, the partition is not essential.

The cap under consideration can be very readily withdrawn in the same manner as a conventional cap, that is to say by disengaging the needle 2 from this latter in a movement of translation in the axial direction. However, by virtue of the special design of the present cap, this latter can subsequently be put back in position very easily after the needle has been used, without thereby entailing any danger of accidental pricking and resultant contamination.

Figure 5:
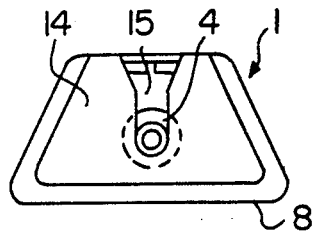
FIG. 5 is a view in elevation of that end of the present cap which is adjacent to a syringe when placed in position.

By virtue of the large flat face 8, said cap can then be placed on a flat surface such as a table T as shown in FIG. 5. It is then only necessary to bring the needle 2 into position above the slit 9 of the cap in order to insert it downwards into this latter. During this insertion, the needle 2 momentarily separates the two strips 10 which form a closure valve. The sleeve 4 which exists at the lower end of said needle then in turn separates the two inner locking strips 11 until the sleeve rests against the bearing plate 12. The strips 11 then return to their initial position so as to exert pressure on the sleeve 4 by means of their edges, thus ensuring that the cap 11 is securely fixed in position on the needle 2.

Thus the operator does not need to use both hands in order to put the cap 1 back in position since this latter can accordingly be placed on a table T or any other desired flat support. Moreover, there is no attendant danger of mishandling since it is only necessary to position the needle 2 above the face 9 and then to insert it downwards between the two series of strips 10 and 11 until it reaches its final position. In consequence, the medical practitioner is in no way liable to sustain injury during this operation since he or she accordingly holds the syringe 3 in one hand without having to hold the cap 1 with the other hand as is necessarily the case with protective caps of current designs.

A further advantage of the present cap lies in the fact that the needle 2 placed within said cap is securely maintained within this latter and enclosed by the two pairs of fastening and enclosing strips 10 and 11 without entailing any need to add any closure member. Now this is also essential in order to guard against any danger of accidental pricking and contamination.

It is worthy of note that the cap in accordance with the invention is not limited to the single example of construction described in the foregoing. Said cap could thus have a cross-section other than a cross-section of trapezoidal shape. If so required, this cross-section could be of rectangular or square shape. In an extreme case, said cap could even have a circular or elliptical cross-section having a flat portion constituting its large bearing face 8. As already mentioned, the resilient clip 13 could be dispensed with if necessary. However, the position of said clip could also be modified since this latter could be so arranged as to be located on the other side with respect to the annular flange 6 provided at the base of the cone 4 which serves as a support for the needle. Many other alternative forms of construction of the protective cap in accordance with the invention could in any case be contemplated.

What is claimed is:

1. A protective cap for the needle of an injection syringe having at its base a mounting sleeve, said cap being comprised by a hollow elongated body open at one end and having along all its length a longitudinal opening (9) for the lateral introduction of the needle (2) of a syringe (3) through the corresponding side of said hollow body, on the side opposite this longitudinal opening (9), said elongated body (1) having a flat baring surface (8) permitting resting said body in a stable position on a flat surface, along opposite sides of the longitudinal opening (9) said body having flexible strips which are inwardly inclined, said strips being adapted both to let a used needle (2) of a syringe pass between them during its introduction through said opening (9) and to exert pressure thereafter on said mounting sleeve (4) at the base of the needle (2) so as to immobilize the needle, and two other flexible strips (10) which cover the first-mentioned said strips and form a valve for closing said opening.

2. A protective cap according to claim 1, wherein the cross section of said cap has a quadrangular contour having a long base which corresponds to the flat bearing face of said cap which is located on the side opposite to the longitudinal opening.

3. The protective cap according to claim 1, wherein a resilient clip is provided near the open end of said cap in order to receive and lock the sleeve which exits at the lower end of a hypodermic needle.

4. A protective cap according to claim 1, further comprising a partition having a slot near the open end of said cap.

* * * * *